United States Patent
Järverud et al.

(10) Patent No.: US 7,228,172 B2
(45) Date of Patent: Jun. 5, 2007

(54) BI-VENTRICULAR PACER, SYSTEM AND METHOD

(75) Inventors: Karin Järverud, Solna (SE); Nils Holmström, Järfälla (SE); Anders Björling, Järfälla (SE); Asa Uhrenius, Stockholm (SE); Sven-Erik Hedberg, Kungsängen (SE); Göran Budgifvars, Spanga (SE); Hans Strandberg, Sundbyberg (SE)

(73) Assignee: St. Jude Medical AB, Jarfalla (SE)

( * ) Notice: Subject to any disclaimer, the term of this patent is extended or adjusted under 35 U.S.C. 154(b) by 393 days.

(21) Appl. No.: 10/734,767

(22) Filed: Dec. 13, 2003

(65) Prior Publication Data
US 2004/0127951 A1 Jul. 1, 2004

(30) Foreign Application Priority Data
Dec. 16, 2002 (SE) .................... 0203727

(51) Int. Cl.
*A61N 1/368* (2006.01)
(52) U.S. Cl. ............................ 607/9; 607/28
(58) Field of Classification Search ............ 607/9, 607/15, 27; 600/509, 528

See application file for complete search history.

(56) References Cited

U.S. PATENT DOCUMENTS

| 4,955,376 | A | | 9/1990 | Callaghan et al. | |
|---|---|---|---|---|---|
| 5,720,768 | A | | 2/1998 | Verboven-Nelissen | |
| 6,070,100 | A | | 5/2000 | Bakels et al. | |
| 6,148,234 | A | * | 11/2000 | Struble ................ | 607/28 |
| 6,456,881 | B1 | | 9/2002 | Bornzin et al. | |
| 2001/0012953 | A1 | * | 8/2001 | Molin et al. ............ | 607/9 |
| 2001/0049542 | A1 | * | 12/2001 | Florio et al. ............ | 607/28 |
| 2003/0083711 | A1 | * | 5/2003 | Yonce et al. ............ | 607/27 |

FOREIGN PATENT DOCUMENTS

| EP | 0 990 451 | 4/2000 |
|---|---|---|
| EP | 1 023 919 | 8/2000 |

\* cited by examiner

*Primary Examiner*—George R. Evanisko
*Assistant Examiner*—Michael Kahelin
(74) *Attorney, Agent, or Firm*—Schiff Hardin LLP

(57) ABSTRACT

An implantable bi-ventricular heart stimulating device and system, suitable for treating congestive heart failure, have a control circuit with first and second pacing circuits and first and second sensing circuits. The device operates with time cycles corresponding to normal heart cycles. The control circuit determines: (a) whether a signal typical of an evoked response to a pacing pulse delivered by the first pacing circuit is sensed within a first time interval and (b) whether a signal typical for an R-wave transferred from the second ventricle, or from some other part of the heart, to the first ventricle is detected within a first time window. The operation of the device depends on whether the conditions (a) and (b) are fulfilled.

21 Claims, 2 Drawing Sheets

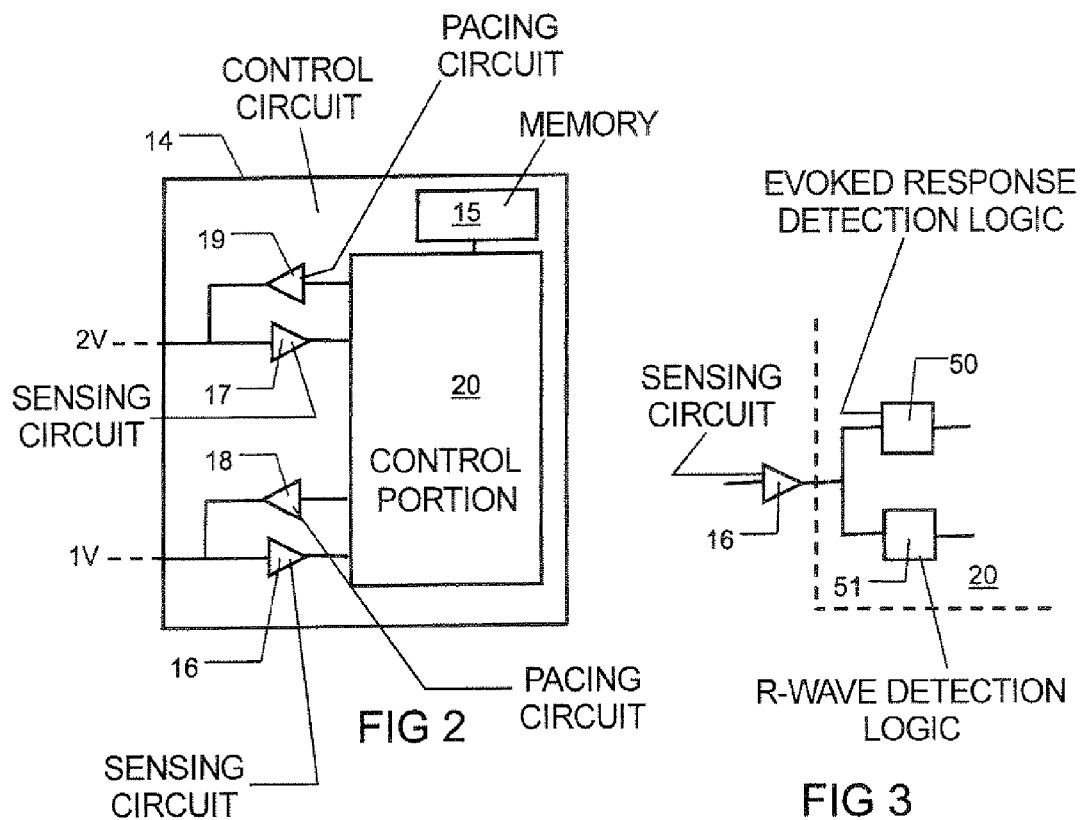
FIG 2
FIG 3
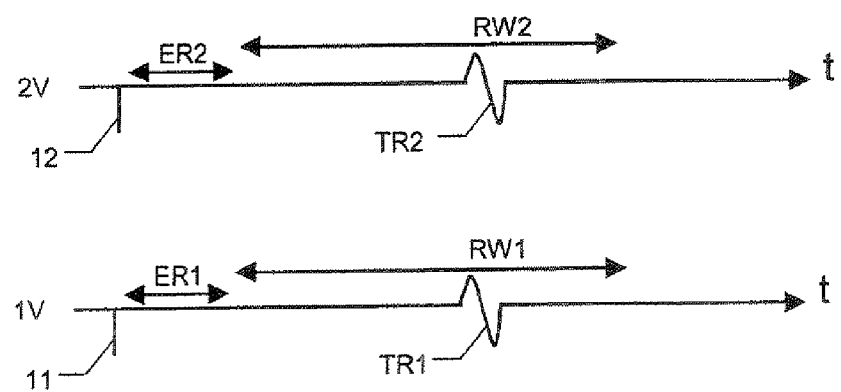
FIG 4

BI-VENTRICULAR PACER, SYSTEM AND METHOD

BACKGROUND OF THE INVENTION

1. Field of the Invention

The present invention relates to an implantable heart-stimulating device with which it is possible to stimulate both the ventricles of a heart, i.e. a bi-ventricular pacemaker or defibrillator (pacer).

The invention also relates to a system including such a device and to the use of the system.

2. Description of the Prior Art

Several different implantable devices for stimulating a heart are known. Such devices normally are able to sense electrical activity of the heart. Some implantable devices are able to deliver stimulation pulses to both the left and right ventricles of the heart, and sometimes also to the left and right atria.

Devices that are able to deliver stimulation pulses to both the left and right ventricles are called bi-ventricular pacers. Such devices can be used to treat patients who suffer from different severe cardiac problems, e.g. patients suffering from congestive heart failure (CHF). CHF is defined generally as the inability of the heart to deliver a sufficient amount of blood to the body. CHF can have different causes. For example, it can be caused by a left bundle branch block (LBBB) or a right bundle branch block (RBBB). By using bi-ventricular pacing, the contraction of the ventricles can be controlled in order to improve the ability of the heart to pump blood. The stimulation pulses to the two ventricles can be delivered simultaneously, but it is also known to deliver the stimulation pulses to the two ventricles with a short time delay between them in order to optimize the pumping performance of the heart.

U.S. Pat. No. 5,720,768 describes different possible electrode positions in order to stimulate or sense the different chambers of the heart.

U.S. Pat. No. 6,070,100 describes positioning the electrodes in both the left and the right atrium as well as in the left and the right ventricles.

In connection with implantable pacers, in particular pacers which only have the possibility to stimulate the right ventricle, and sometimes also the right atrium, it is known to detect capture of the heart, i.e. to detect whether the heart actually reacts to a delivered stimulation pulse. If the heart is not captured the pacer delivers a back-up pulse with a higher pulse energy than the first pulse. It is also possible to increase the pulse energy of future stimulation pulses if capture is not detected. In order to save battery capacity it is important that the stimulation pulses are not delivered with an unnecessarily high energy. By varying the energy of the stimulation pulses and by detecting capture it is possible to find a threshold value for the stimulation pulse energy. Based on the threshold value, a suitable stimulation pulse energy can be determined.

The detection of capture involves several problems. Different signals from the heart or generated by the pacemaker may interfere with each other, which may make the detection of capture difficult. The evoked response that it is intended to detect may thus be hidden because of other electrical phenomena. It is particularly difficult to detect capture in a bi-ventricular pacer, because in such a pacer there are more delivered and detected signals which may interfere with each other.

U.S. Pat. No. 6,148,234 describes a system for detecting capture in connection with bi-ventricular or bi-atrial pacing. This patent describes the fact that if a chamber is captured, there is a biological refractory period during which this chamber cannot be stimulated again. The system described in this patent monitors these refractory periods for the different chambers, for example for the two ventricles. When capture is achieved in both ventricles, no intrinsic depolarization signals can be sensed during the following refractory period. However, where the output level of one of the pacing pulses is insufficient to capture one ventricle, but capture is achieved in the other ventricle, a delayed depolarization pattern can be detected in the ventricle that was not captured. This delayed depolarization is due to an interventricular conduction from the ventricle that is captured to the ventricle that is not captured. The system according to this patent thus monitors the refractory interval following each delivery of stimulating pulses to the ventricles. A loss of capture is indicated in case such a delayed depolarization is sensed during the refractory period.

Also United States Patent Application Publication 2001/0049542 describes a system for detecting capture in connection with bi-ventricular or bi-atrial stimulation. The system includes a morphology detector incorporated in a micro-controller to allow for the processing of the sensed intra-cardiac electrogram signals (IEGM). The morphology of the IEGM may depend on whether both the ventricles (or atria) have captured or not. By detecting the shape of the IEGM capture may thus, be detected.

Another concept used in this technical field is "fusion". Fusion may occur when an intrinsic depolarization of the heart takes place simultaneously, or substantially simultaneously, with a stimulation pulse from the heart-stimulating device.

SUMMARY OF THE INVENTION

The present invention concerns in particular an implantable heart stimulating device including a first pacing circuit adapted to be connected to a first pacing electrode suited to be positioned in or at a first ventricle of a heart and to receive signals from the first pacing circuit pace the first ventricle, a first sensing circuit adapted to be connected to a first sensing electrode suited to be positioned in or at the first ventricle of the heart and to transfer signals to the first sensing circuit to sense the first ventricle, a second pacing circuit adapted to be connected to a second pacing electrode suited to be positioned in or at a second ventricle of the heart and to receive signals from the second pacing circuit to pace the second ventricle, a second sensing circuit adapted to be connected to a second sensing electrode suited to be positioned in or at the second ventricle of the heart and to transfer signals to the second sensing circuit to sense the second ventricle, and a control circuit.

The control circuit and the first sensing circuit are arranged to be able to detect a signal typical of an evoked response to a pacing pulse delivered by the first pacing circuit, by sensing within a first time interval that follows after a pacing pulse delivered by the first pacing circuit.

The control circuit and the first sensing circuit are being arranged to be able to detect, within a first time window, a signal of the kind typical for an R-wave transferred from the second ventricle, or from some other part of the heart, to the first ventricle. This first time window is not identical to the first time interval.

The control circuit is operable with time cycles corresponding to normal heart cycles. If, within one such time cycle, pacing pulses are delivered both by the first pacing circuit and by the second pacing circuit, then these pacing pulses are considered by the control circuit to have been delivered substantially simultaneously.

It should be noted that "substantially simultaneously" as used herein means that the pacing pulses are exactly simultaneous or that there is only a short time between them. The pacing pulses ought to be delivered substantially simultaneously so that the pacing pulse delivered by the second pacing circuit does not interfere with the detection of an evoked response to a pacing pulse delivered by the first pacing circuit. It should also be noted that pacing pulses will not necessarily be delivered both by the first pacing circuit and the second pacing circuit during every time cycle, since it is also possible that the delivery of a pacing pulse is inhibited.

In connection with the above-described device it may be difficult to distinguish a loss of capture in a ventricle from a situation in which fusion occurs. In a fusion beat, some cardiac cells already have been activated by a spontaneous depolarization taking place substantially simultaneously with a pacing pulse. The evoked response signal can be weaker than if fusion were not present. Consequently, the first sensing circuit may not detect any evoked response even though the ventricle in question has been depolarized during the fusion beat.

It is an object of the present invention to provide an implantable heart stimulating device of the above kind with which it is possible to distinguish the occurrence of a real loss of capture from a fusion situation, and wherein the operation of the device is controlled in accordance therewith. A further object is to provide such a device which is relatively uncomplicated and which can be implemented by relatively simple circuit.

The above objects are achieved by an implantable heart monitoring device of the above described kind, wherein the control circuit:
  (a) determines whether, during a time cycle, the aforementioned signal typical of an evoked response to a pacing pulse delivered by the first pacing circuit is sensed within the first time interval,
  (b) determines whether during the same time cycle the aforementioned signal of the kind typical for an R-wave transferred from the second ventricle, or from some other part of the heart, to the first ventricle is detected within the first time window, and the control circuit operates the device dependent on whether the conditions (a) and (b) are fulfilled.

By determining the conditions (a) and (b) it is possible to determine whether a fusion beat has occurred. Since the operation of the device preferably should be different in the situation where fusion occurs as opposed to the situation when a real loss occurs, the control circuit operates the device appropriately dependent on whether the conditions (a) and (b) are fulfilled. The operation of the device thus may be optimized to the actually occurring condition.

The term "real loss" as used herein circuit that the ventricle in question has not been depolarized, i.e. no capture has occurred, and that also no fusion has occurred.

Preferably, the control circuit operates the device in a manner L1 if it is the case both that the condition (a) is not fulfilled and that the condition (b) is fulfilled, and in another manner F1 if it is the case both that the condition (a) is not fulfilled and that the condition (b) is not fulfilled. The manner L1 means that the device functionally operates as if a real loss of capture has occurred in the first ventricle and the manner F1 circuit that the device functionally operates as if a fusion has occurred in the first ventricle. If the condition in (a) is not fulfilled, this means that no evoked response has been detected by the first sensing circuit. This can be due either to a real loss of capture or to fusion. If the situation (b) is fulfilled, this means that a transferred R-wave has been detected by the first sensing circuit. This occurs only if the first ventricle was not depolarized. Consequently, this situation indicates that a real loss of capture has occurred. Analogously, in case no such transferred R-wave is detected, this indicates that probably a fusion situation exists. It should be noted that the labels L1 and F1 are used only to distinguish the manners from each other.

In an embodiment, if a real loss of capture (i.e. L1) has been determined a predetermined number of times, then the control circuit varies the energy of the pacing pulses delivered by the first pacing circuit and detects, via the first sensing circuit, signals typical for evoked responses during the first time interval such that a suitable pulse energy for the pacing pulses delivered by the first pacing circuit is determined. If a real loss is the case, it is thus advantageous to do a threshold search in order to determine a suitable pulse energy.

According to another embodiment, if fusion (i.e. F1) has been determined a predetermined number of times, then the control circuit modifies at least one time period that controls the operation of the device. This time period can be either increased or decreased. One possibility is to increase the time period. If the time period is increased, then a possible stimulation pulse is delivered later. Thus the stimulation pulse is less likely to interfere with the intrinsic depolarization, i.e. the risk for fusion decreases. It is possible to decrease the time period such that a possible stimulation pulse is delivered earlier. Also in this case the risk for fusion decreases.

The aforementioned first time interval can start 0–30 ms after the delivery of a pacing pulse by the first pacing circuit and can be between 25 ms and 100 ms long. The aforementioned first time window can start between 0 ms and 150 ms after the delivery of the pacing pulse by the first pacing circuit. The first time window preferably ends at least before 400 ms after the delivery of the pacing pulse by the first pacing circuit. These times have been found to be suitable for detecting an evoked response and a transferred R-wave, respectively. In an embodiment, the first time window does not start before the end of the first time interval.

In another preferred embodiment, the control circuit also
  (c) determines whether, during a time cycle, the signal typical of an evoked response to a pacing pulse delivered by the second pacing circuit is sensed within a second time interval,
  (d) determines whether during the same time cycle, the signal of the kind typical for an R-wave transferred from the first ventricle, or from some other part of the heart, to the second ventricle is detected within a second time window, and the control circuit operates the device also dependent on whether the conditions in (c) and (d) are fulfilled. Thereby the above described advantages are also achieved in connection with the second pacing and sensing circuit.

In to this embodiment, real loss can be distinguished from fusion also with regard to the other ventricle. With regard to this other ventricle, the control circuit can operate in a manner corresponding to the embodiments described above.

The invention also is directed to an implantable heart stimulating system having a device according to any of the above embodiments and a first lead and a second lead connected to the device. The first pacing electrode is arranged on the first lead and the second pacing electrode is arranged on the second lead. Preferably, the first sensing electrode is the same electrode as the first pacing electrode and the second sensing electrode is the same electrode as the second pacing electrode. With such a system, the advantages described above are achieved.

The invention also is directed to the use of such a system. According to this use, the system is implanted in a human or animal, and the first pacing electrode is positioned in or at a first ventricle of the heart of the human or animal and the second pacing electrode is positioned in or at the second ventricle of the heart. The system preferably is used to treat a human or animal suffering from congestive heart failure, for due to example a bundle branch block.

DESCRIPTION OF THE DRAWINGS

FIG. 2 schematically shows a control circuit which may form part of the device.

FIG. 3 schematically shows a somewhat more detailed illustration of part of the control circuit of FIG. 2.

FIG. 4 schematically shows on a time scale signals related to first and second pacing and sensing circuits.

DESCRIPTION OF PREFERRED EMBODIMENTS

Figure 1:
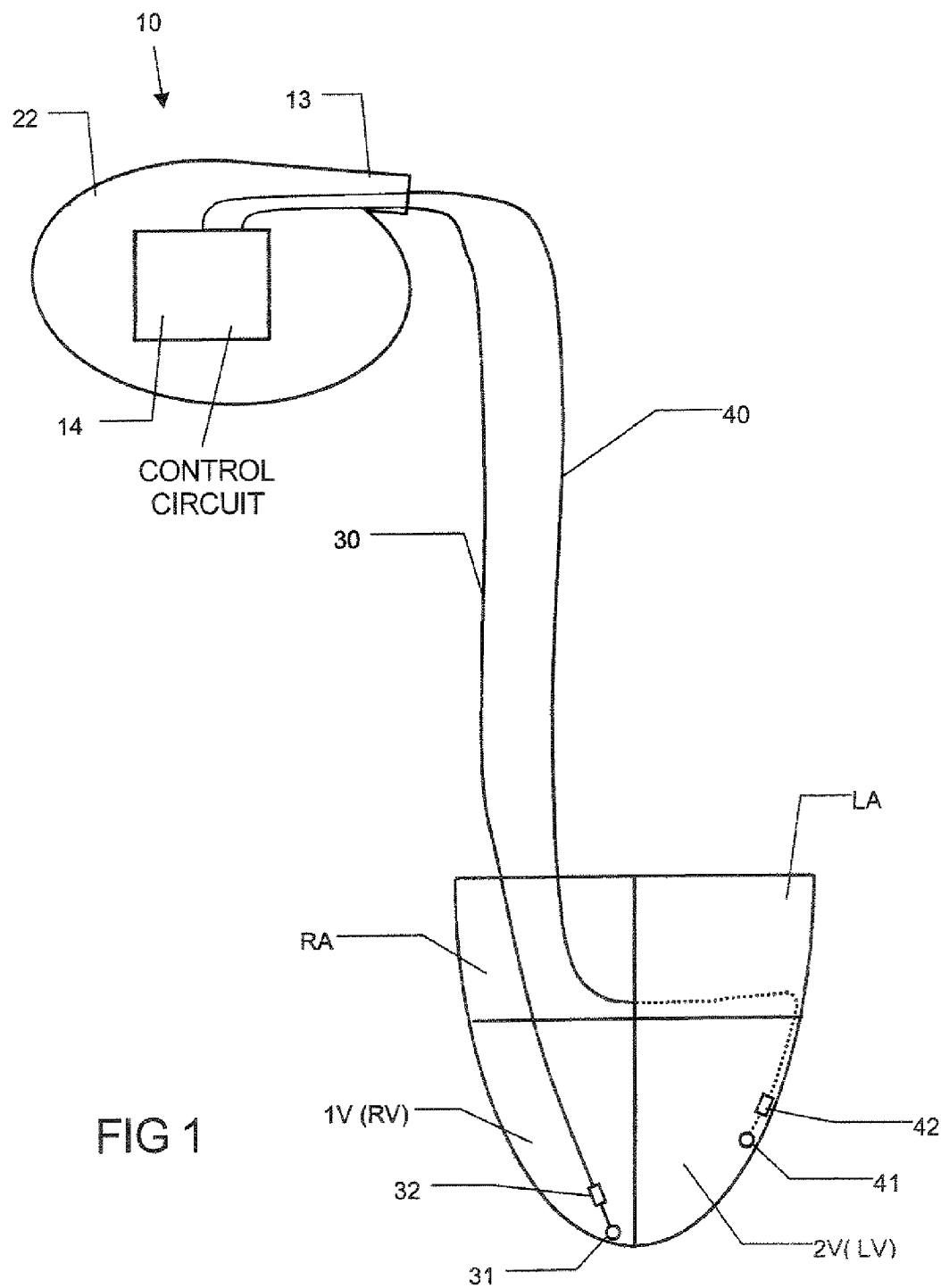
FIG. 1 schematically shows a heart stimulating system with a heart stimulating device connected to leads with sensing and pacing electrodes positioned in a heart.

FIG. 1 schematically shows an implantable heart stimulating device 10 according to the invention. The device 10 has a housing 22. The housing 22 contains a control circuit 14. The device 10 also has a connector portion 13. Via the connector portion 13, the device 10 can be connected to different leads. In FIG. 1 the device 10 is connected to a first lead 30 and to a second lead 40. The device 10 together with the first lead 30 and the second 40 lead constitute an implantable heart stimulating system according to the invention. The first lead 30 includes a pacing tip electrode 31 and a sensing electrode pair 31, 32. In this shown example this electrode pair 31, 32 is a bipolar lead with a tip portion 31 and a ring portion 32. However, it is within of the scope of the invention to instead use unipolar leads, as is known to those skilled in the art. The second lead 40 has a corresponding electrode pair 41, 42.

FIG. 1 also schematically illustrates a heart with a right atrium RA, a left atrium LA, a first ventricle 1V (which in this case is the right ventricle RV) and a second ventricle 2V (which in this case is the left ventricle LV). The electrodes 31, 32 are positioned in the first ventricle 1V in order to be able to pace and sense this ventricle 1V. The electrodes 41, 42 are positioned so as to pace and sense the second ventricle 2V. The second lead 40, for example, may be introduced via the right atrium RA and the coronary sinus such that the electrodes 41, 42 are positioned in for example the middle or great cardiac vein of the heart. (Normally the left ventricular lead is forwarded beyond the great cardiac vein until its electrodes are somewhere in a coronary vein). How to introduce the lead 40 in this manner is known to those skilled in the art. Although not shown in FIG. 1, it is also possible for the system to be connected to further leads with electrodes positioned in order to sense and/or pace the right atrium RA and the left atrium LA.

FIG. 2 schematically shows the control circuit 14 in more detail. The control circuit 14 includes a memory 15 connected to a control portion 20. The control circuit 14 has a first pacing circuit 18. The circuit 18 is adapted to be connected to the first pacing electrode pair 31, 32, which, as shown in FIG. 1, is positioned so as to receive signals from the first pacing circuit 18 such that the first pacing circuit 18 is able to pace the first ventricle 1V. The control circuit 14 also includes a first sensing circuit 16. The first sensing circuit 16 is adapted to be connected to the first sensing electrode pair 31, 32, which can be positioned in the first ventricle 1V in order to transfer signals to the first sensing circuit 16. In this manner, the first sensing circuit 16 is able to sense the first ventricle 1V. Although the first pacing electrode could be a different electrode from the first sensing electrode, it is preferred that the same electrodes 31, 32 is used both for pacing and sensing.

The control circuit 14 also includes a second pacing circuit 19 adapted to be connected to a second pacing electrodes 41, 42 for pacing the second ventricle 2V of the heart. The control circuit 14 also includes a second sensing circuit 17 adapted to be connected to the second sensing electrodes 41, 42 in order to be able to sense the second ventricle 2V of the heart. The second pacing electrode is preferably the same electrode as the second sensing electrode. The control circuit 14 may of course also include means for pacing and sensing the atria of the heart.

FIG. 4 schematically shows events related to the first ventricle 1V and the second ventricle 2V on a time scale. The marker 11 represents a pacing pulse delivered by the first pacing circuit 18 and the marker 12 represents a pacing pulse delivered by the second pacing circuit 19.

The control circuit 14 and the first sensing circuit 16 are arranged to be able to detect a signal typical of an evoked response to a pacing pulse 11 delivered by the first pacing circuit 18 by sensing within a first time interval ER1.

According to a preferred embodiment, the control circuit 14 and the second sensing circuit 17 are also arranged to be able to detect a signal typical of an evoked response to the pacing pulse 12 delivered by the second pacing circuit 19 by sensing within a second time interval ER2. How to arrange the control circuit 14 in order to detect an evoked response is known to a person skilled in the art. The first time interval ER1 may be set, for example, to begin 15 ms after the delivery of a pacing pulse 11 by the first pacing circuit 18. The length of the first time interval ER1 may for example be 50 ms. Analogously, the second time interval ER2 may start 15 ms after the delivery of a pacing pulse 12 by the second pacing circuit 19 and may have a length of about 50 ms.

The control circuit 14 and the first sensing circuit 16 are also arranged to be able to detect, within a first time window RW1, a signal of the kind typical for an R-wave TR1 transferred from the second ventricle 2V, or from some other part of the heart, to the first ventricle 1V. The first time window RW1 is not identical with the first time interval ER1. As described above, if for example the first ventricle 1V is depolarized, then this ventricle 1V will be in the biological refractory period during for example about 350 ms after the ventricle 1V was depolarized. During this biological refractory period, the first ventricle 1V cannot be depolarized again. However, if the first ventricle 1V was not depolarized but the second ventricle 2V was depolarized, then, the depolarization of the second ventricle 2V will via the myocardium reach the first ventricle 1V and may be detected as a delayed depolarization of the first ventricle 1V. It is also possible that a transferred R-wave TR1 can originate from some other part of the heart, such as from the A-V-node. Such a transferred R-wave TR1 can be detected within the first time window RW1. The time it takes for such a transferred R-wave TR1 to be sensed by the first sensing circuit 16 depends on the particular case. The control circuit 14 defines the first time window RW1 such that it is suitable for detecting a transferred R-wave TR1 in the particular case. The first time window RW1 may start, for example, 80 ms after the delivery of a pacing pulse by the first pacing circuit 18. The first time window RW1 may be, for example, 200 ms long. According to an alternative embodiment, the first time window RW1 can start directly after the delivery of a pacing pulse 11 by the first pacing circuit 18. However, according to a preferred embodiment the first time window RW1 does not start before the end of the first time interval ER1. It should be noted that the first time window RW1 coincides with the point in time when a pacing pulse, such as a back-up pulse, is delivered by the second pacing circuit 19, then the sensing of a transferred R-wave TR1 preferably should be disabled for a short time around such a point in time. In other words: the time window RW1 should in this case include a short blanking period during which the sensing of a transferred R-wave is not possible.

According to a preferred embodiment, the control circuit 14 and the second sensing circuit 17 are also arranged to be able to detect, within a second time window RW2, a signal of the kind typical for an R-wave TR2 transferred from the first ventricle 1V, or from some other part of the heart, to the second ventricle 2V. The second time window RW2 is not identical with the second time interval ER2. Analogously to the description above, the second time window RW2 can start, for example, 80 ms after the delivery of a pacing pulse by the second pacing circuit 19. The second time window RW2 may be, for example, 200 ms long. Although it is possible for the second time window RW2 to start immediately after the delivery of a pacing pulse 12 by the second pacing circuit 19, according to a preferred embodiment the second time window RW2 does not start before the end of the second time interval ER2. Also the second time window RW2 preferably includes a blanking period if a back-up pulse is delivered by the first pacing circuit 18 during the second time window RW2.

It should be noted that the circuit arrangement for detecting an evoked response preferably is different from the arrangement for detecting other signals, such as a transferred R-wave TR1, TR2. FIG. 3 shows schematically a part of the control circuit 14 in more detail. FIG. 3 illustrates that the first sensing circuit 16 is connected to evoked response detection logic 50 and R-wave detection logic 51. The detection logics 50 and 51 can be seen to form part of the control portion 20 illustrated in FIG. 2. Preferably, similar detection logics are arranged also for the second sensing circuit 17. The detection logic 50 is optimized to sense an evoked response and the detection logic 51 optimized to detect an R-wave. The detection logic 50 thus is active during the first time interval ER1 and the detection logic 51 is active during the first time window RW1. It is possible for the first time window RW1 to overlap with the first time interval ER1 if the detection logics 50, 51 are sufficiently different to distinguish the different signals from each other. In particular, it is in this case important to be able to distinguish a transferred R-wave TR1 from a signal typical of a fusion beat. However, according to a preferred embodiment, the first time window RW1 does not overlap with the first time interval ER1. The second time window RW2, according to one embodiment, does not overlap with the second time interval ER2.

The control circuit 14 is arranged to be able to operate with time cycles corresponding to normal heart cycles. Such an operation is normal for an implantable heart stimulating device. The time cycle is determined by preset timer intervals which also may depend on detected signals.

The control circuit 14 can be arranged such that pacing pulses are delivered both by the first pacing circuit 18 and the second pacing circuit 19 during each time cycle. However, it is also possible for the control circuit 14 to inhibit the delivery of pacing pulses by the first pacing circuit 18 and/or the second pacing circuit 19 as is known to those skilled in the art. Nevertheless, if pacing pulses are delivered both by the first pacing circuit 18 and the second pacing circuit 19 during a time cycle, then these pacing pulses are considered to have been delivered substantially simultaneously. If this were not the case, but, for example, a pacing pulse 12 was delivered by the second pacing circuit 19 during the first time interval ER1, then it would be difficult to detect an evoked response to a pacing pulse 11 delivered by the first pacing circuit 18. The pacing pulses delivered by the first pacing circuit 18 and the second pacing circuit 19 therefore should be delivered substantially simultaneously such that the pacing pulses do not fall within the first or second time intervals ER1, ER2.

According to the invention, the control circuit:
(a) determines whether during a time cycle a signal typical of an evoked response to a pacing pulse 11 delivered by the first pacing circuit 18 is sensed within the first time interval ER1, and
(b) determines whether during the same time cycle a signal typical of an R-wave TR1 transferred from the second ventricle 2V, or from some other part of the heart, to the first ventricle 1V is detected within the first time window RW1. The control circuit 14 operates the device 10 dependent on whether the conditions (a) and (b) are fulfilled.

If the condition (a) is not fulfilled and the condition (b) is fulfilled, this is an indication of a real loss of capture in the first ventricle 1V. The control circuit 14 then will operate the device 10 in a manner L1. This manner L1 may include, for example, storage of an indication in the memory 15 that a loss of capture in the first ventricle 1V has been detected. When such a loss has been determined a predetermined number of times (which can be 1, 2 or any number of times), then the control circuit 14 can vary the energy of the pacing pulses 11 delivered by the first pacing circuit 18 in order to perform a threshold search for finding a suitable energy for the pacing pulses. How to perform such a threshold search is known to those skilled in the art and therefore will not be described in more detail herein.

If, on the other hand, the condition (a) is not fulfilled and also the condition (b) is not fulfilled, then this is an indication of the fact that fusion probably has occurred. The control circuit 14 is thereby arranged to operate the device 10 in another manner F1. This manner F1 may involve, for example, storage of an indication in the memory 15 that such fusion has been detected. Furthermore, if fusion has been detected a predetermined number of times (which can be 1, 2 or any number of times) then the control circuit 14 modifies a time period that controls the operation of the device 10. Depending on the operational mode of the device 10, the control circuit 14 can, for example, increase the escape interval or increase the A-V or P-V interval. This measure circuit that a stimulation pulse (if generated) will be delivered later in time. Thus the probability of fusion decreases. If the device 10 is set to operate in an inhibition mode, this circuit that the intrinsic depolarization is more likely to be sensed such that a pacing pulse can be inhibited.

It should also be noted that when the control circuit 14 is arranged to sense a possible transferred R-wave TR1 during the first time window RW1, then the control circuit 14 preferably causes no backup pulse to be delivered during the time cycle in question, at least not by the first pacing circuit 18, since such a back-up pulse could interfere with a detection of the transferred R-wave TR1.

According to a preferred embodiment, the control circuit 14 carries out steps corresponding to those described above with regard to the second ventricle 2V. In other words: the control circuit 14

(c) determines whether during a time cycle a signal typical of an evoked response to a pacing pulse delivered by the second pacing circuit 19 is sensed within the second time interval ER2, and (d) determines whether during the same time cycle a signal typical for an R-wave TR2 transferred from the first ventricle 1V, or from some other part of the heart, to the second ventricle 2V is detected within the second time window RW2.

The control circuit 14 operates the device 10 dependent on whether the conditions (c) and (d) are fulfilled.

If the condition (c) is not fulfilled and the condition (d) is fulfilled, then the control circuit 10 operates in a manner L2, i.e. in a manner suitable if a real loss of capture has occurred in the second ventricle 2V. The device 10 can then perform a threshold search of the same kind as described above in order to find a suitable pulse energy for the pacing pulses delivered by the second pacing circuit 19.

If the condition (c) is not fulfilled and the condition (d) also is not fulfilled, then the device 10 is operated in another manner F2, i.e. a manner which is based on the assumption that a fusion has occurred in the second ventricle 2V. The control circuit 14 can operate such that a time period is increased in an analogous manner to the above description in connection with the first ventricle 1V.

The table below shows an example of decisions made by the device 10 on how to interpret the different signals detected and the pulses delivered.

| DETECTION | DECISION | |
|---|---|---|
| | FIRST VENTRICLE | SECOND VENTRICLE |
| L1, C2, TR1, — | Real loss | Capture |
| L1, C2, —, — | Fusion | Capture |
| C1, L2, —, TR2 | Capture | Real loss |
| C1, L2, —, — | Capture | Fusion |
| i1, L2, —, TR2 | Inhibition | Real loss |
| i1, L2, —, — | Inhibition | Fusion |
| L1, i2, TR1, — | Real loss | Inhibition |
| L1, i2, —, — | Fusion | Inhibition |
| i1, C2, —, — | Inhibition | Capture |
| C1, i2, —, — | Capture | Inhibition |

In the table, 1 refers to the first ventricle 1V (and thereby to the first pacing circuit 18 and the first sensing circuit 16). 2 refers to the second ventricle 2V (and thereby to the second pacing circuit 19 and the second sensing circuit 17). L means that no evoked response is sensed during the respective time interval ER1 or ER2. C means that an evoked response is sensed during the time interval ER1 or ER2. i refers to inhibition, i.e. that during the time cycle in question no pacing pulse has been delivered by the pacing means in question. In the first column (Detection) the first position thus refers to the first ventricle 1V and the second position refers to the second ventricle 2V. The third position concerns the detection of a signal typical for a transferred R-wave to the first ventricle 1V during the first time window RW1, i.e. the detection of a signal TR1. A hyphen (-) in this position means that no such signal TR1 has been detected. Analogously, the fourth position concerns the second ventricle 2V and the question whether a transferred signal TR2 is detected during the time window RW2.

The second and third columns in the table indicate how the signals are functionally interpreted by the device 10. In particular the difference between a real loss and a fusion as has been described above can be found in the table. The device 10 is thus operated in accordance with the decisions in the table. Those skilled in the art know how the device is suitably arranged to operate in response to the different situations such as real loss, fusion, capture and inhibition.

The invention also concerns the use of an implantable heart stimulating system of the kind illustrated in FIG. 1. The system is implanted in a human or animal and the first pacing electrodes 31, 32 are positioned in or at the first ventricle 1V and the second pacing electrodes 41, 42 are positioned in or at the second ventricle 2V as described above. Preferably, the system is used to treat a human or animal suffering from congestive heart failure, for example caused by a bundle branch block.

Although modifications and changes may be suggested by those skilled in the art, it is the intention of the inventors to embody within the patent warranted hereon all changes and modifications as reasonably and properly come within the scope of their contribution to the art.

We claim:

1. A method for treating a subject by biventricular cardiac stimulation comprising the steps of:

in a subject suffering from congestive heart failure, implanting a housing containing a first pacing circuit that generates pacing pulses having an energy, a first sensing circuit, a second pacing circuit that generates pacing pulses having an energy, a second sensing circuit, and a control circuit connected to said first and second pacing circuits and to said first and second sensing circuits;

implanting a first pacing electrode to interact with a first ventricle of a heart of the subject and connecting said first pacing electrode to said first pacing circuit to receive signals from the first pacing circuit to pace the first ventricle with said pacing pulses generated by said first pacing circuit;

implanting a first sensing electrode to interact with the first ventricle of the heart of the subject and connecting said first sensing electrode to the first sensing circuit to transfer signals to the first sensing circuit to sense the first ventricle;

implanting a second pacing electrode to interact with a second ventricle of the heart of the subject and connecting said second pacing electrode to said second pacing circuit to receive signals from the second pacing circuit to pace the second ventricle said pacing pulses generated by said second pacing circuit;

implanting a second sensing electrode suited to interact with the second ventricle of the heart of the subject and connecting said second sensing electrode to the second sensing circuit to transfer signals to the second sensing circuit to sense the second ventricle;

with said control circuit and the first sensing circuit, detecting a signal typical of an evoked response to a pacing pulse delivered by the first pacing circuit, by sensing within a first time interval that follows after a pacing pulse delivered by the first pacing circuit;

with said control circuit and said first sensing circuit, also detecting, within a first time window, a signal typical for an R-wave transferred from the second ventricle, or from some other part of the heart, to the first ventricle, wherein said first time window is not identical with the first time interval;

operating the control circuit with time cycles corresponding to normal heart cycles and, in the control circuit, if within one of said time cycles pacing pulses are delivered both by the first pacing circuit and by the second pacing circuit, determining these pacing pulses to have been delivered substantially simultaneously;

in said control circuit, distinguishing between a real loss of capture and fusion by
(a) determining whether during a time cycle the signal typical of an evoked response to a pacing pulse delivered by the first pacing circuit is sensed within the first time interval, and
(b) determining whether during the same time cycle the signal of the kind typical for an R-wave transferred from the second ventricle, or from some other part of the heart, to the first ventricle is detected within the first time window, and operating at least said first and second pacing circuits with said control circuit differently dependent on respective combinations of fulfillment and non-fulfillment of (a) and fulfillment and non-fulfillment of (b).

2. A method as claimed in claim 1 comprising implanting said housing, said first and second pacing electrodes, and said first and second sensing electrode in a living subject suffering from a bundle branch block.

3. A method according to claim 1 comprising the steps of:
with said control circuit and said second sensing circuit, detecting a signal typical of an evoked response to a pacing pulse delivered by the second pacing circuit, by sensing within a second time interval that follows after a pacing pulse delivered by the second pacing circuit;
with said control circuit and said second sensing circuit detecting, within a second time window, a signal of the kind typical for an R-wave transferred from the first ventricle, or from some other part of the heart, to the second ventricle, wherein this second time window is not identical with the second time interval;
in said control circuit, also distinguishing between a real loss of capture and fusion by
(c) determining whether during a time cycle the signal typical of an evoked response to a pacing pulse delivered by the second pacing circuit is sensed within the second time interval, and
(d) determining whether during the same time cycle the signal of the kind typical for an R-wave transferred from the first ventricle, or from some other part of the heart, to the second ventricle is detected within the second time window; and
operating at least said first and second pacing circuits with said control circuit differently also dependent on respective combinations of fulfillment and non-fulfillment of (c) and fulfillment and non-fulfillment of (d).

4. A method according to claim 1 comprising, through said control circuit, operating at least said first and second pacing circuits in a first manner if both (a) is not fulfilled and (b) is fulfilled, and in a second manner if both (a) is not fulfilled and (b) is not fulfilled.

5. A method according to claim 4 comprising, in said first manner, operating at least said first and second pacing circuits as if a real loss of capture has occurred in the first ventricle and, in said second manner, as if fusion has occurred in the first ventricle.

6. A method according to claim 5 comprising, through said control circuit, if both (a) not being fulfilled and (b) being fulfilled has occurred a predetermined number of times, varying the energy of the pacing pulses delivered by the first pacing circuit and detecting, with the first sensing circuit, signals typical for evoked responses during the first time interval to determine a suitable pulse energy for the pacing pulses delivered by the first pacing circuit.

7. A method according to claim 5 comprising, through said control circuit, if both (a) not being fulfilled and (b) not being fulfilled has occurred a predetermined number of times, modifying at least one time period that controls the operation of at least said first and second pacing circuits.

8. A method according to claim 7 comprising, through said control circuit, modifying said time period by increasing or decreasing said time period.

9. A method according to claim 1 comprising, through said control circuit, starting said first time interval 0–3 ms after delivery of a pacing pulse by the first pacing circuit and setting said first time interval to be between 25 ms and 100 ms long.

10. A method according to claim 9, comprising starting said first time window between 0 ms and 150 ms after the delivery of the pacing pulse by the first pacing circuit.

11. A method according to claim 9 comprising, through said control circuit, ending said first time window at least before 400 ms after the delivery of the pacing pulse by the first pacing circuit.

12. A method according to claim 9 comprising, through said control circuit, including a blanking window in said first time window in which sensing of an R-wave transferred from said second ventricle, or from some other part of the heart, is precluded.

13. A method according to claim 3 comprising, through said control circuit, operating at least said first and second pacing circuits in a first manner if both (c) is not fulfilled and (d) is fulfilled, and in a second manner if both (c) is not fulfilled and (d) is not fulfilled.

14. A method according to claim 13 comprising, in said first manner, operating at least said first and second pacing circuits as if a real loss of capture has occurred in the second ventricle and, in said second manner, as if a fusion has occurred in the second ventricle.

15. A method according to claim 14 comprising, through said control circuit, if both (c) not being fulfilled and (d) being fulfilled has occurred a predetermined number of times, varying the energy of the pacing pulses delivered by the second pacing circuit and detecting, with the second sensing circuit, signals typical for evoked responses during the second time interval to determine a suitable pulse energy for the pacing pulses delivered by the second pacing circuit.

16. A method according to claim 14 comprising, through said control circuit, if both (c) not being fulfilled and (d) being not fulfilled has occurred a predetermined number of times, modifying at least one time period that controls operation of at least said first and second pacing circuits.

17. A method according to claim 16 comprising, through said control circuit, modifying said time period by increasing or decreasing said time period.

18. A method according to claim 1 comprising, through said control circuit, starting said first time interval 0–3 ms after delivery of a pacing pulse by the first pacing circuit and setting said first time interval to be between 25 ms and 100 ms long.

19. A method according to claim 18, comprising starting said first time window between 0 ms and 150 ms after the delivery of the pacing pulse by the first pacing circuit.

20. A method according to claim 18 comprising, through said control circuit, ending said first time window at least 400 ms after the delivery of the pacing pulse by the first pacing circuit.

21. A method according to claim 18 comprising, through said control circuit, including a blanking window in said first time window in which sensing of an R-wave transferred from said second ventricle, or from some other part of the heart, is precluded.

* * * * *